(12) United States Patent
Silpachai et al.

(10) Patent No.: US 7,037,272 B2
(45) Date of Patent: May 2, 2006

(54) INFANT RESPIRATORY MONITORING SYSTEM

(76) Inventors: Ohlan Silpachai, 9949 Basswood Ct., Ventura, CA (US) 93004; Michael Karst, 1890 W. Hillcrest Dr. #498, Newbury Park, CA (US) 91320

( * ) Notice: Subject to any disclaimer, the term of this patent is extended or adjusted under 35 U.S.C. 154(b) by 63 days.

(21) Appl. No.: 10/899,539

(22) Filed: Jul. 26, 2004

(65) Prior Publication Data

US 2006/0020221 A1    Jan. 26, 2006

(51) Int. Cl.
*A61B 5/08* (2006.01)
(52) U.S. Cl. ........................... 600/538; 600/529
(58) Field of Classification Search ............... 600/529, 600/549, 531–538, 21, 22
See application file for complete search history.

(56) References Cited

U.S. PATENT DOCUMENTS

| | | | | |
|---|---|---|---|---|
| 5,190,048 A | * | 3/1993 | Wilkinson | 600/537 |
| 5,251,636 A | * | 10/1993 | Neuman | 600/537 |
| 5,676,154 A | * | 10/1997 | Pettersson | 600/532 |
| 6,011,477 A | * | 1/2000 | Teodorescu et al. | 340/573.1 |
| 6,165,133 A | * | 12/2000 | Rapoport et al. | 600/529 |
| 6,368,287 B1 | * | 4/2002 | Hadas | 600/529 |
| 2003/0171686 A1 | * | 9/2003 | Gannon | 600/532 |
| 2003/0199780 A1 | * | 10/2003 | Page | 600/538 |

* cited by examiner

*Primary Examiner*—Robert L. Nasser
*Assistant Examiner*—Navin Natnithithadha

(57) ABSTRACT

The present invention provides a method and apparatus for monitoring infant respiration during sleep. More specifically, the present invention alerts the caregiver when an infant has ceased to breathe during sleep. The usefulness of such device applies to Sudden Infant Death Syndrome (SIDS) and prolonged apnea leading to a life threatening event. One embodiment of a method according to the present invention comprises monitoring the relative level of humidity from an infant respiration and comparing it to the room ambient relative humidity. A determination is made when an infant has stopped breathing once the level of the humidity from the infant breaths approaches the room humidity level. At such time, the present invention provides an alert to the caregiver to allow appropriate actions to be taken in reviving or waking the infant as applicable.

8 Claims, 6 Drawing Sheets

INFANT RESPIRATORY MONITORING SYSTEM

BACKGROUND OF THE INVENTION

1. Field of the Invention

One of a new parent's worst fears is to discover that their newborn had stopped breathing during sleep and died. Despite inadequate explanations for deaths resulting from Sudden Infant Death Syndrome (SIDS), many believe that apnea may be a precursor of SIDS. The standard definition of infancy apnea is cessation of inspiratory gas flow for 20 seconds, or for a shorter period of time if accompanied by bradycardia (heart rate less than 100 beats per minute), cyanosis, or pallor. Although there has been no proven correlation between apnea and Sudden Infant Death Syndrome (SIDS), many parents still demand an in-home device to monitor their newborns and babies as indicated by the availability of infant monitoring systems offered in the market.

Respiration cessations of infants are normal, yet a pause lasting longer than 20 seconds is a cause for alarm. Once 20 second of apnea is exceeded, the baby may begin to turn blue or pale, choke or gag, and go limp. A prolonged apnea that does not result in death is officially called Apparent Life-Threatening Event (ALTE). Infants and babies can be saved if ALTE is detected promptly[i]. The mean postmenstrual age for SIDS occurrence is estimated to be 45.8 weeks for infants born at 24 to 28 weeks gestation, compared with 52.3 weeks for full term infants.[ii] Current evidence suggests that if cardio-respiratory monitoring is elected, it usually may be discontinued after 43 weeks' postmenstrual age although extreme apnea may persist beyond that time in some infants.[iii] The present invention relates to in-home infant respiration monitoring systems and more specifically to apnea monitoring systems for newborns up to the postmenstrual age of 52 weeks.

[i] Infant Apnea Monitors Help Parents Breath Easy, Dori Stehlin, FDA Consumer Magazine.

[ii] Malloy M H, Hoffman H J. Prematurity, sudden infant death syndrome and age of death. Pediatrics. 1995; 96:464–471

[iii] Apnea, Sudden Infant Death Syndrome, and Home Monitoring; American Academy of Pediatrics, Policy Statements; Organizational Principles to Guide and define the Child Health Care System and/or Improve the Health of All Children, Committee on Fetus and Newborn. Pediatrics. April 2003, Vol. 111 No. 4

2. Description of the Related Art

Devices for in-home infant and baby monitoring range from a simple audio monitoring system to a more complex video monitoring system and to one of the more popular patented methods, the Respiration and Movement Monitoring System (U.S. Pat. No. 6,011,477). This method utilizes "accelerometric" sensors contained in the bedding an infant lies on and detects the infant's movement. It relies on the simple logic that a moving infant is a living infant. This apparatus is intended to monitor movement generated by a breathing infant and alerts caregivers when movement ceases. However, this method does not directly measure the infant's actual breath or lack thereof, but indirectly detects respiration through associated movement. Another similar indirect method, Optical Monitor For Sudden Infant Death Syndrome (U.S. Pat. No. 6,492,634), also monitors the infant's movement using a complex light source in conjunction with an optical device to create a matrix of images. A more precise method for determining infant or newborn respiratory stage should include the detection of the breath itself. The present invention does this that by providing a method and an apparatus for monitoring the humidity resulting from infant respiration.

SUMMARY OF THE INVENTION

The relative humidity (RH) from respiring humans including infants is significantly higher than that of a controlled room. The American Society of Heating, Refrigerating and Air Conditioning Engineers recommend that in winter indoor temperatures be maintained between 68 and 76 degrees Fahrenheit, and in summer indoor temperatures be maintained between 73 and 80 degrees Fahrenheit. Relative humidity levels should be maintained between 30 and 60 percent. The present invention monitors the infant respiration humidity level and compares this level to room ambient RH level to ascertain the infant respiratory stage. The present invention determines that the monitored infant respiration has ceased when the RH from the infant's breath falls to the level of room ambient RH within a pre-established amount of time, and provides an apparatus to warn caregivers when the monitored infant's respiration ceases. A further object of this invention is to provide a method and apparatus to monitor respiration of an infant without physical attachments to the subject being monitored.

The invention includes at least one relative humidity (RH) sensor (U.S. Pat. No. 6,724,612) for measuring humidity level in the monitored infant's breath, and a reference (RH) sensor for measuring the room ambient relative humidity. In addition, the present invention includes a respiratory antenna (Unpatented) for directing the path of the subject's breaths to the RH sensors such that humidity measurement is optimized. A controller (Unpatented) processes signals from the RH sensor exposed to the subject's breaths and compares this level to the room ambient humidity from the reference RH sensor over a specified period of time and provides a warning alarm when the humidity of both sensors are processed to be within a specified threshold in a pre-established time period. An optional receiver provides remote warnings through the reception of RF signals sent by the controller.

The features and advantages of the invention will be apparent, taken together with the accompanying drawings.

BRIEF DESCRIPTION OF THE DRAWINGS

DRAWING 1 depicts a view of an infant with an isometric front view of the apparatus used to monitor the infant's respiratory pattern;

DRAWING 2 is an isometric front view of the apparatus showing the locations of the RH sensors intended to directly monitor an infant's respiration;

Figure 1:
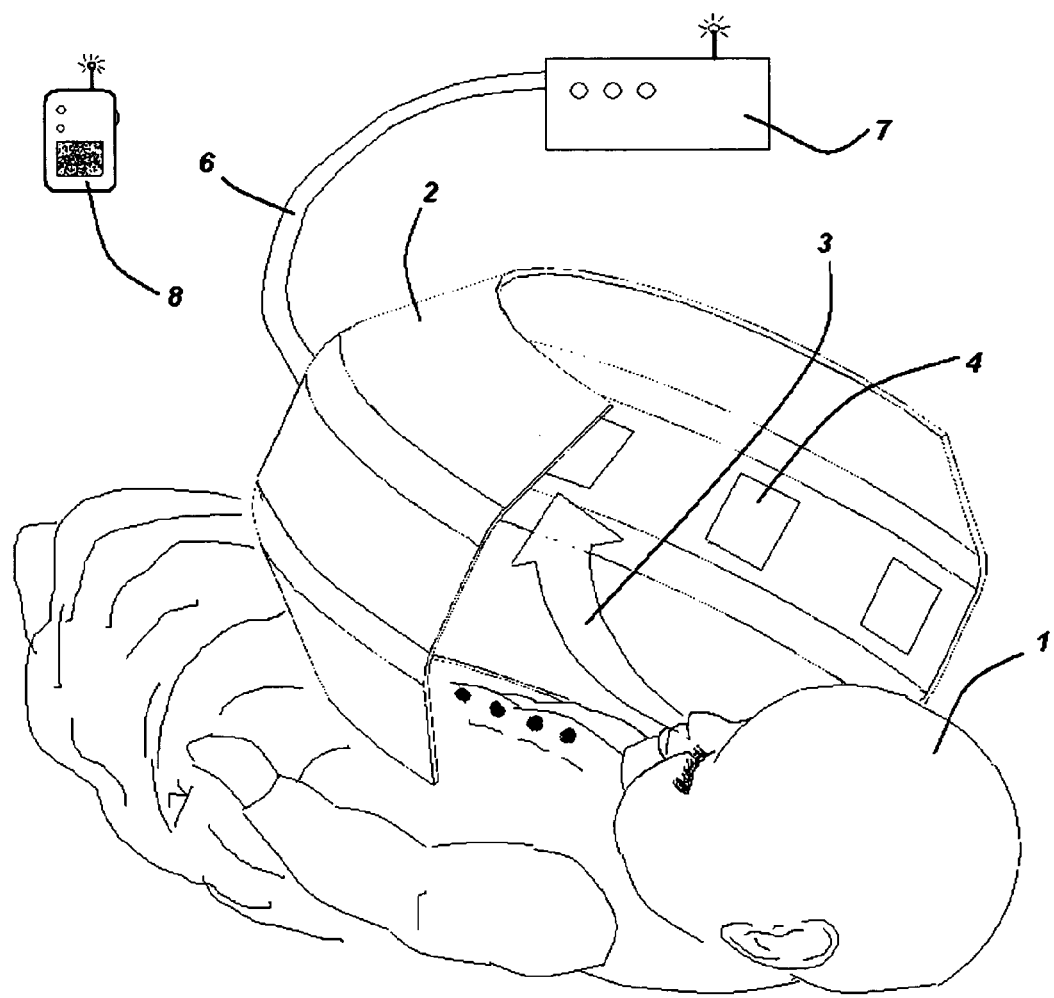
Figure 2:
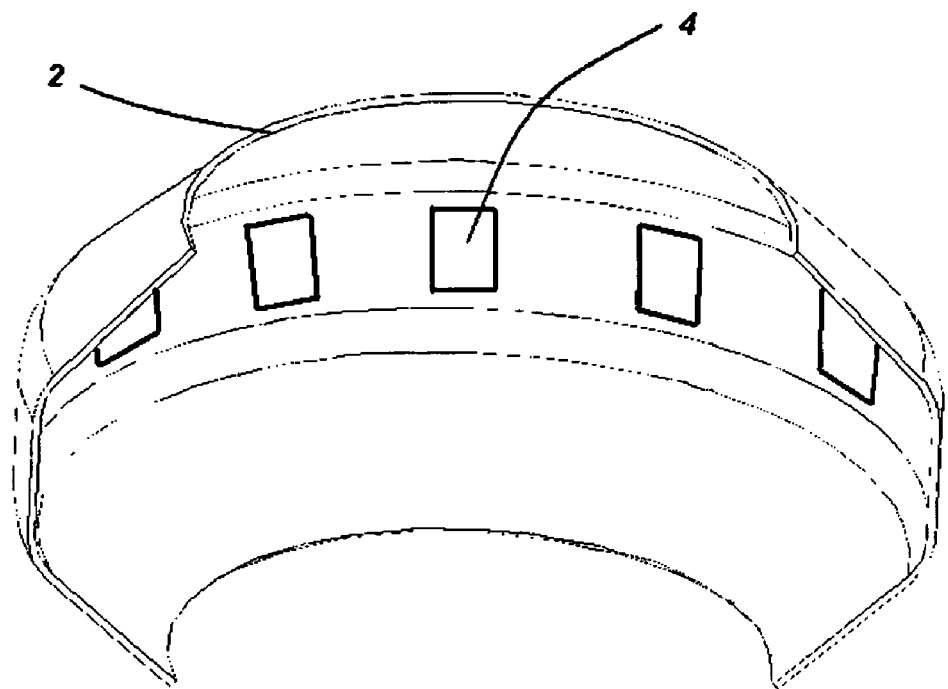
Figure 3:
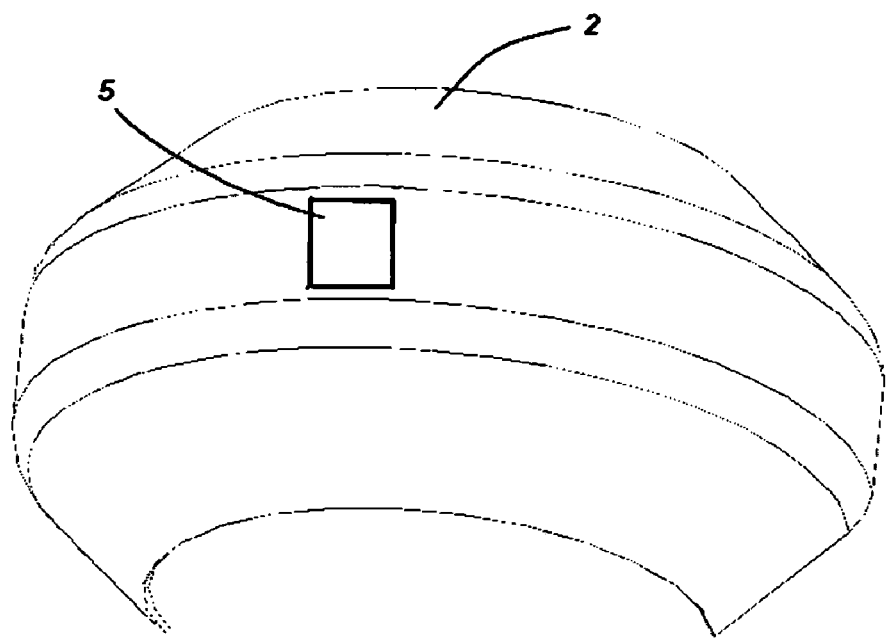
Figure 4:
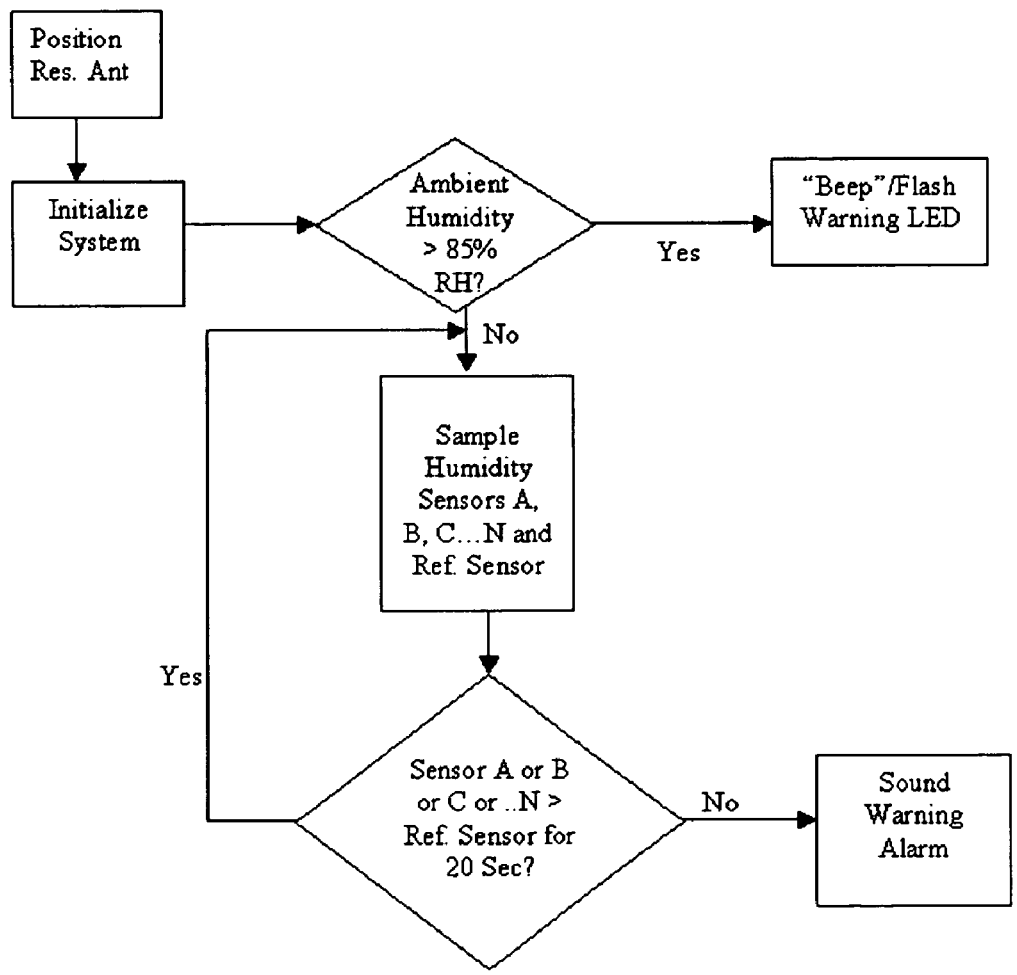
Figure 5:
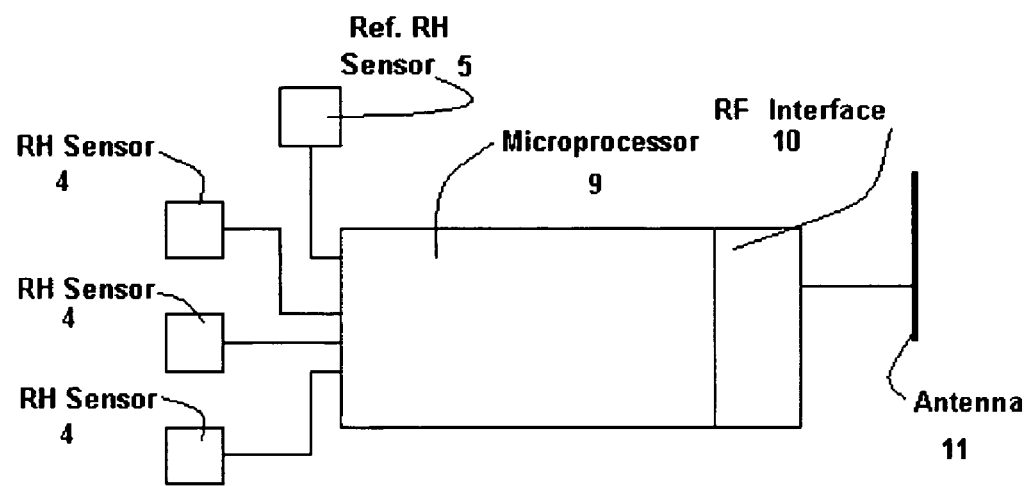
Figure 6:
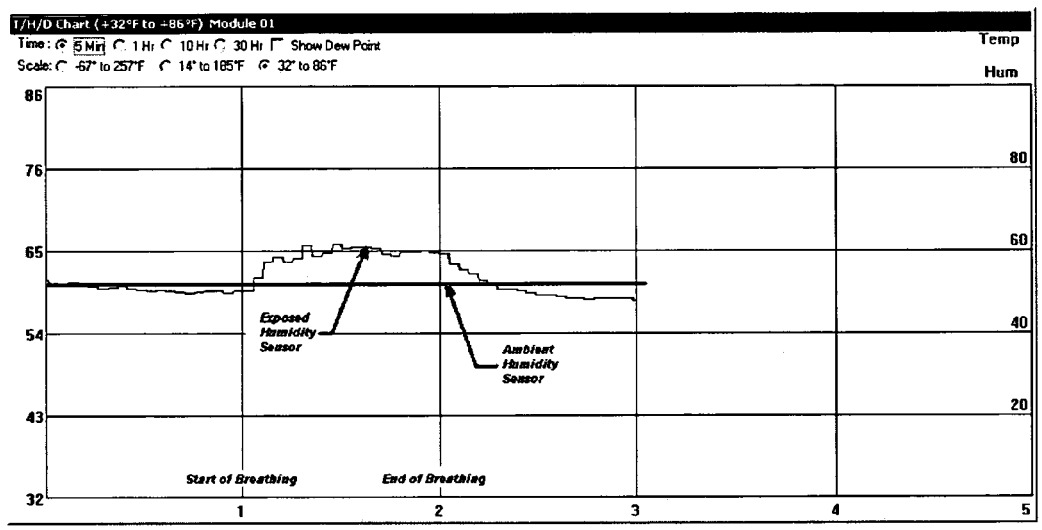

DRAWING 3 is an isometric back view of the apparatus showing the location of the reference RH sensor;

DRAWING 4 is a simplified processing diagram;

DRAWING 5 is a simplified electrical diagram of the controller;

DRAWING 6 is a graph depicting an adult breathing pattern with data recorded from a prototype device.

DETAILED DESCRIPTION OF THE INVENTION

DRAWING 1 shows one embodiment of an infant respiration monitoring system includes; respiratory antenna 2, RH sensors 4, flexible tube 6, controller 7, and an optional remote receiver 8. In DRAWING 1, an infant 1 respiration 3 is directed by the preferred shape of the respiratory antenna 2 into the RH sensors 4 placed strategically in of the respiratory antenna 2. The respiratory antenna 2 is optimally positioned to capture the infant respiration 3 by adjustments made in the flexible tube 6. The relative humidity from infant 1 respiration 3 is measured by the RH sensors 4 and processed by the controller 7.

DRAWING 2 shows the preferred locations of the RH sensors 4 on the respiratory antenna 2. In this embodiment, the sensors 4 are placed into an arc following the possible movement of the infant's nose as the head may rotate from side to side.

DRAWING 3 shows the location of the reference RH sensor 5 on the backside of the preferred shape of the respiratory antenna 2 where it is not directly exposed to the humidity of the infant respiratory. Signals from the reference RH sensor 5 are compared to signals from the RH sensors 4 placed inside the respiratory antenna 2 by the controller 7.

DRAWING 4 shows a simplified processing diagram the controller 7 uses to determine when the monitored infant 1 or newborn respiration ceases for more than 20 seconds. Once the respiratory antenna 2 has been placed in the preferred position to maximize capturing the infant's 1 respiration 3, the caregiver initializes the system. The controller 7 verifies that the ambient humidity is less than 85% RH and sounds a warning alarm if the ambient humidity falls below this level rendering the present invention ineffective. The humidity from a respiring human, including infants are in the range of 92% RH to 99% RH. Ambient room humidity over 85% does not permit the present invention to accurately assess the difference between the humidity from a monitored subject and room ambient humidity. Once the controller 7 has determined that the ambient humidity is less than 85% RH, the controller 7 begins and continues to sample signals from the RH sensors 4 as well as the reference ambient RH sensor 5. As the monitored infant 1 breathes into the respiratory antenna 2, relative humidity from the breath is detected by at least one of the RH sensor 4 and the controller 7 samples its signal. At any time, at least one of the sensors 4 detects the infant's breath depending on the infant's head orientation. The sensor 4 most directed to the respiration path will detect the highest humidity signal. The controller 7 also samples humidity level from the reference RH sensor 5 and compares this level to the RH sensors 4. In a controlled room condition, the humidity value from at least one of the RH sensor 4 is significantly higher than the reference sensor 5. The controller 7 interprets this condition as acceptable and continues to sample the signals. However, in the event that the infant experiences apnea, its respiratory function ceases and the humidity level detected by at least one of the RH sensor 4 rapidly declines. If the level continues to drop, it will eventually be equal to the level of the reference RH sensor 5. As this happens, the controller 7 interprets this condition as Apparent Life-Threatening Event and sounds an alarm to warn the caregiver that an immediate attention is needed.

DRAWING 5 is a simplified architecture of the controller 7. At least one RH sensor 4 (3 shown) and one reference RH sensor 5 are monitored by a microprocessor 9. In the preferred embodiment, an RF interface 10 is also included with an antenna 11 to provide alert to the remote receiver 8 as shown in DRAWING 1.

DRAWING 6 illustrates the present invention monitoring capability of human respiratory stages. These plots were made from the original prototype of the present invention monitoring respiratory stages of an adult male subject. Point "1" on the horizontal axis is the point at which the subject started to breathe into the respiratory antenna. Point "2" is the point at which breath is purposely held to mimic apnea. The blue signal line is one from a RH sensor 4 while the black line is from an ambient RH sensor 5. As DRAWING 6 indicates, at point "1", relative humidity read by the sensor 4 increased until breathing was held to mimic apnea at point "2" where the signal rapidly declined. After about 10 seconds, the relative humidity level from the RH sensor 4 is equal or below the level of the reference RH sensor.

Although the present invention has been described in considerable detail with reference to certain preferred configuration thereof, other versions are possible. For example, the respiratory antenna 2 can be any shape that guides the respiration 3 of an infant 1 and directs it to the RH sensor 5. The reference RH sensor 5 can be located anywhere in the same proximity of the monitored infant 1 as long as it is not directly exposed to the infant 1 respiration 3. The controller 7 need not be as described in DRAWING 5 but any suitable technology that can be used to interpret either analog or digital output of a RH sensor 4 or 5 and provide a comparison to a reference sensor is acceptable.

We claim:

1. An apparatus that does not require physical attachment to an infant for monitoring respiration by measuring relative humidity, RH level from the monitored infant or baby comprising:
    a respiratory antenna to guide and direct the infant respiration to at least one RH sensor;
    at least one RH sensor captivated in the respiratory antenna to monitor the relative humidity level associated with an infant respiration;
    a reference ambient RH sensor to monitor the ambient room humidity level;
    a controller to process the RH sensors signals, compares the difference between at least one RH sensor and the reference RH sensor, determine acceptable ambient humidity level of operation, and provide an alert when a specified condition is met.

2. A method of claim 1, wherein a monitored infant's respiration is guided to at least one strategically located RH sensor to maximize the humidity signal strength.

3. A method of claim 1, wherein the respiratory antenna can be positioned to maximize the detection of the monitored infant respiration even when the infant's head moves from side to side.

4. A method of claim 1, wherein the humidity level from the monitored infant's respiration is detected by at least one RH sensor captivated in the respiration antenna.

5. A method of claim 1, wherein a reference RH sensor detects the ambient relative humidity of a controlled room where the monitored infant rests.

6. A method of claim 1, wherein the controller compares the signals from at least on RH sensor and an ambient reference RH sensor to determine if the monitored infant respiration has ceased for more than 20 seconds.

7. A method of claim 1, wherein the controller alerts the caregiver through a remote RF receiver in the event the monitored infant respiration has ceased for more than 20 seconds.

8. A system for monitoring an infant's respiratory condition, comprising: a respiratory antenna for channeling the monitored infant respiration; and at least one RH sensor for monitoring relative humidity of the infant's breath; and one reference RH sensor for monitoring the ambient room relative humidity; a flexible tube for positioning the respiratory antenna; a controller to sample, analyze RH sensors signals, and provide alert to the caregiver; and a remote RF receiver for providing remote warning to the caregiver.

* * * * *